United States Patent [19]

Breckenridge

[11] 4,101,597
[45] Jul. 18, 1978

[54] RECOVERY OF P-XYLENE AND BENZENE FROM EIGHT CARBON ATOM AROMATIC FRACTIONS

[75] Inventor: Lloyd L. Breckenridge, Philadelphia, Pa.

[73] Assignee: Mobil Oil Corporation, New York, N.Y.

[21] Appl. No.: 809,231

[22] Filed: Jun. 23, 1977

[51] Int. Cl.$^2$ ............................ C07C 5/24; C07C 3/62; C07C 7/01
[52] U.S. Cl. .............................. 260/668 A; 260/672 T; 260/674 A
[58] Field of Search ............ 260/674 A, 672 T, 668 A

[56] References Cited

U.S. PATENT DOCUMENTS

| 3,856,872 | 12/1974 | Morrison | 260/668 A |
| 3,945,913 | 3/1976 | Brennan et al. | 260/672 R |
| 3,957,621 | 5/1976 | Bonacci et al. | 260/674 A |

Primary Examiner—Delbert E. Gantz
Assistant Examiner—C. E. Spresser
Attorney, Agent, or Firm—Charles A. Huggett; Raymond W. Barclay

[57] ABSTRACT

Recovery of valuable components from eight carbon atom ($C_8$) aromatic fractions is enhanced by high temperature processing of $C_9^+$ aromatics produced by side reactions during isomerization of a $C_8$ aromatics fraction lean in p-xylene and resulting from separation of that isomer from a mixture of the three xylene isomers and ethyl benzene.

5 Claims, 1 Drawing Figure

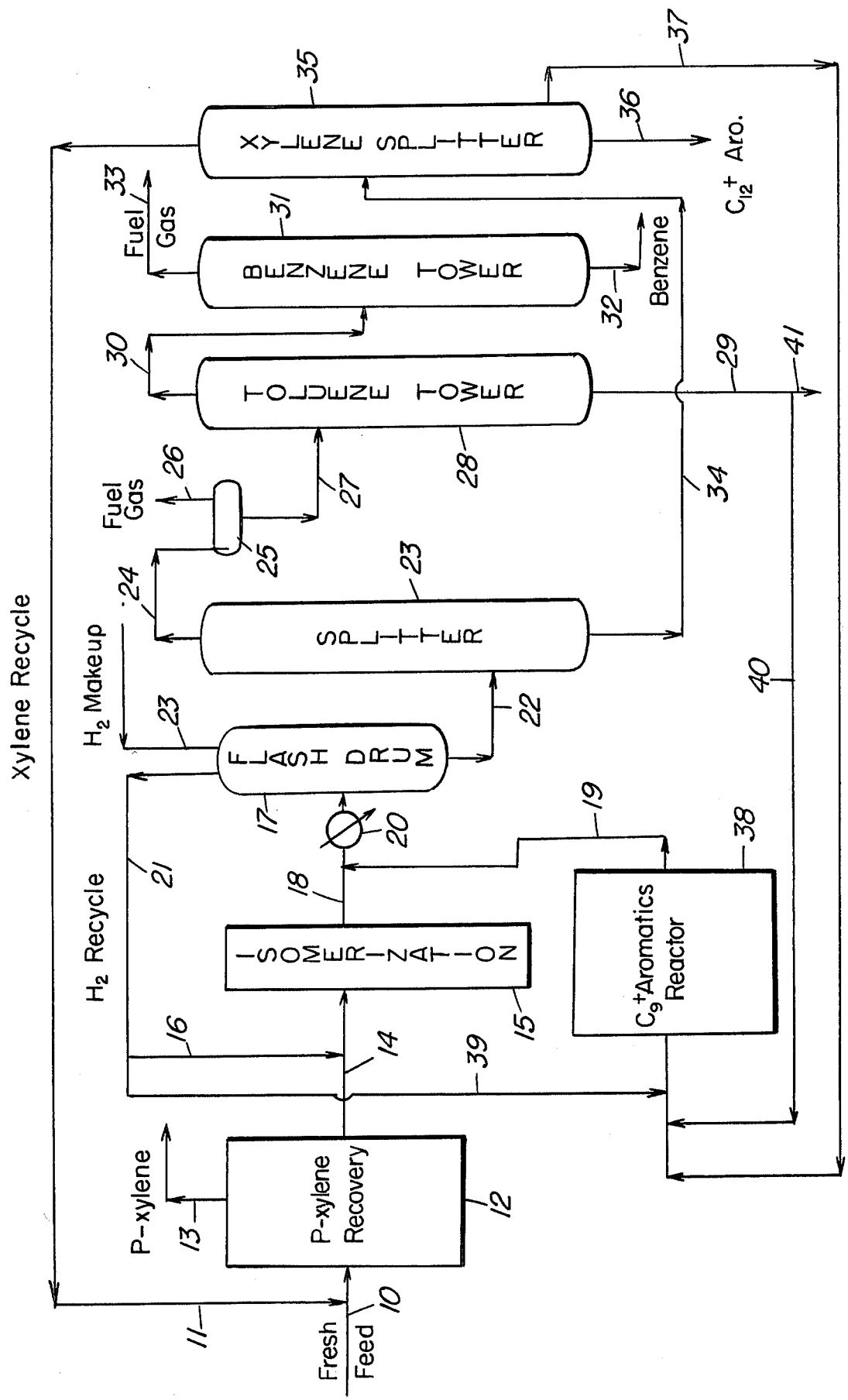

RECOVERY OF P-XYLENE AND BENZENE FROM EIGHT CARBON ATOM AROMATIC FRACTIONS

BACKGROUND OF THE INVENTION

Of the aromatic compounds used in industry, benzene and xylenes are of outstanding importance on a volume basis. Those compounds are derived primarily from such aromatic naphthas as petroleum reformates and pyrolysis gasolines. The former result from processing petroleum naphthas over a catalyst such as platinum on alumina at temperatures which favor dehydrogenation of naphthenes. Pyrolysis gasolines are liquid products resulting from mild hydrogenation (to convert diolefins to olefins without hydrogenation of aromatic rings) of the naphtha fraction from steam cracking of hydrocarbons to manufacture ethylene, propylene, etc.

Regardless of aromatic naphtha source, it is usual practice to extract the liquid hydrocarbon with a solvent highly selective for aromatics to obtain an aromatic mixture of the benzene and alkylated benzenes present in the aromatic naphtha. That aromatic extract may then be distilled to separate benzene, toluene and $C_8$ aromatics from higher boiling compounds in the extract. The benzene and toluene are recovered in high purity but the $C_8$ fraction, containing valuable para xylene, is a mixture of the three xylene isomers with ethyl benzene. Techniques are known for separating p-xylene by fractional crystallization with isomerization of the other two isomers for recycle in a loop to the p-xylene separation. That operation is hampered by the presence of ethyl benzene (EB). However, a widely used xylene isomerization technique, "Octafining" can be applied. Octafining by passing the $C_8$ aromatics lean in p-xylene and mixed with hydrogen over platinum on silica-alumina not only isomerizes xylenes but also converts ethyl benzene, thus preventing build-up of EB in the separation-isomerization loop.

The manner of producing p-xylene by a loop including Octafining can be understood by consideration of a typical charge from reforming petroleum naphtha. The $C_8$ aromatics in such mixtures and their properties are:

|  | Freezing Point° F. | Boiling Point° F. | Density Lbs./U.S. Gal. |
|---|---|---|---|
| Ethyl benzene | −139.0 | 277.1 | 7.26 |
| P-xylene | 55.9 | 281.0 | 7.21 |
| M-xylene | −54.2 | 282.4 | 7.23 |
| O-xylene | −13.3 | 292.0 | 7.37 |

Principal sources are catalytically reformed naphthas and pyrolysis distillates. The $C_8$ aromatic fractions from these sources vary quite widely in composition but will usually be in the range 10 to 32 wt. % ethyl benzene with the balance, xylenes, being divided approximately 50 wt. % meta, and 25 wt. % each of para and ortho.

Calculated thermodynamic equilibria for the $C_8$ aromatic isomers at Octafining conditions are:

| Temperature | 850° F. |
|---|---|
| Wt. % Ethyl benzene | 8.5 |
| Wt. % para xylene | 22.0 |
| Wt. % meta xylene | 48.0 |
| Wt. % ortho xylene | 21.5 |
|  | 100.0 |

An increase in temperature of 50° F. will increase the equilibrium concentration of ethyl benzene by about 1 wt. %, ortho xylene is not changed and para and meta xylenes are both decreased by about 0.5 wt. %.

Individual isomer products may be separated from the naturally occurring mixtures by appropriate physical methods. Ethyl benzene may be separated by fractional distillation although this is a costly operation. Ortho xylene may be separated by fractional distillation and is so produced commercially. Para xylene is separated from the mixed isomers by fractional crystallization.

As commercial use of para and ortho xylene has increased there has been interest in isomerizing the other $C_8$ aromatics toward an equilibrium mix and thus increasing yields of the desired xylenes.

Isomerization processes operate in conjunction with the product xylene or xylenes separation processes. A virgin $C_8$ aromatics mixture is fed to such a processing combination in which the residual isomers emerging from the product separation steps are then charged to the isomerizer unit and the effluent isomerizate $C_8$ aromatics are recycled to the product separation steps. The composition of isomerizer feed is then a function of the virgin $C_8$ aromatic feed, the product separation unit performance, and the isomerizer performance.

A typical charge to the isomerizing reactor may contain 17 wt. % ethyl benzene, 65 wt. % m-xylene, 11 wt. % p-xylene and 7 wt. % o-xylene. The thermodynamic equilibrium varies slightly with temperature. The objective in the isomerization reactor is to bring the charge as near to theoretical equilibrium concentration as may be feasible consistent with reaction times which do not give extensive cracking and disproportionation.

In Octafining, ethyl benzene reacts through ethyl cyclohexane to dimethyl cyclohexanes which in turn equilibrate to xylenes. Competing reactions are disproportionation of ethyl benzene to benzene and diethyl benzene, hydrocracking of ethyl benzene to ethane and benzene and hydrocracking of the alkyl cyclohexanes.

The rate of ethyl benzene approach to equilibrium concentration in a $C_8$ aromatic mixture is related to effective contact time. Hydrogen partial pressure has a very significant effect on ethyl benzene approach to equilibrium. Temperature change within the range of Octafining conditions (830° to 900° F.) has but a very small effect on ethyl benzene approach to equilibrium.

Concurrent loss of ethyl benzene to other molecular weight products relate to % approach to equilibrium. Products formed from ethyl benzene include $C_8^+$ naphthenes, benzene from cracking, benzene and $C_{10}$ aromatics from disproportionation, and total loss to other than $C_8$ molecular weight. $C_5$ and lighter hydrocarbon by-products are also formed.

The three xylenes isomerize much more selectively than does ethyl benzene, but they do exhibit different rates of isomerization and hence, with different feed composition situations the rates of approach to equilibrium vary considerably.

Loss of xylenes to other molecular weight products varies with contact time. By-products include naphthenes, toluene, $C_9$ aromatics and $C_5$ and lighter hydrocracking products.

Ethyl benzene has been found responsible for a relatively rapid decline in catalyst activity and this effect is proportional to its concentration in a $C_8$ aromatic feed mixture. It has been possible then to relate catalyst stability (or loss in activity) to feed composition (ethyl benzene content and hydrogen recycle ratio) so that for any $C_8$ aromatic feed, desired xylene products can be made with a selected suitably long catalyst use cycle.

Because of its behavior in the loop manufacture of p-xylene, or other xylene isomer, ethyl benzene is undesirable in the feed but is tolerated because of the great expense of removal from mixed $C_8$ aromatics. Streams substantially free of ethyl benzene are available from processes as transalkylation of aromatics having only methyl substituents. Thus toluene can be reacted with itself (the specific transalkylation reaction sometimes called "disproportionation") or toluene may be reacted with tri-methyl benzene in known manner.

The transalkylation reactions provide means for utilizing the higher boiling aromatics separated in preparing BTX from reformates. Thus toluene may be reacted with tri-methyl benzenes to produce xylenes. They are also useful in handling high boiling aromatics formed by side reactions in such processes as isomerization of xylenes.

Another technique for utilizing the $C_9^+$ aromatics is described in U.S. Pat. No. 3,945,913 (Brennan and Morrison) dated Mar. 23, 1976. It is there shown that the alkyl aromatics of nine or more carbon atoms will react over certain acid catalysts exemplified by acid zeolite ZSM-5 to remove alkyl side chains of two or more carbon atoms and equilibrate the remaining methyl benzenes to provide the "BTX" mixture of benzene, toluene and xylenes. As that reaction was further studied, it was found that solid acid catalysts generally will promote the reaction sequence, although such catalysts as silica-alumina, zeolite Y and the like are less attractive than is zeolite ZSM-5 for the purpose. That finding is described and claimed in copending application Ser. No. 774,304, filed Mar. 4, 1977, by Brennan and Morrison.

A recent development in vapor phase isomerization is described in U.S. Pat. No. 3,856,872, (Morrison) dated Dec. 24, 1974. It is there shown that use of a catalyst such as HZSM-5 in combination with a metal having hydrogenation/dehydrogenation promoting capability under essentially Octafining conditions is very efficient for isomerization of xylenes at reduced hydrogen flow as compared with Octafining. The extent of xylene loss is substantially reduced by this change of catalyst. Concurrently, the mechanism of ethyl benzene conversion is drastically changed on substitution of, e.g. NiHZSM-5, for the platinum on silica/alumina of Octafiners. The Morrison process results in conversion of ethyl benzene by transalkylation reactions including disproportionation of ethyl benzene to benzene and diethyl benzene, disproportionation and ethylation of xylene and the like producing alkyl aromatic compounds of nine or more carbon atoms ($C_9^+$) together with benzene and toluene. Those conversion products are readily separated in the loop for recovery of p-xylene and isomerization of o- and m-xylenes. In general, loss of xylenes increases as severity of the isomerizer is increased to enhance the conversion of ethyl benzene.

In Bonacci et al U.S. Pat. No. 3,957,621, dated May 18, 1976, are described various combinations of aromatic processing steps in combination of differing nature.

SUMMARY OF THE INVENTION

Although significant advances have been accomplished as reviewed above, it has now been found that known techniques may be combined in a manner to cause significant increase in efficiency of producing p-xylene from $C_8$ aromatic mixtures including ethyl benzene. That efficiency requires that the known processes be operated within narrow temperature limits.

A vapor phase isomerization unit of the type used in the Morrison process is operated at a temperature of 550° to 700° F. The higher boiling compounds separated from the isomerizer effluent are then processed by the method described in the Brennan and Morrison patent at 750° to 900° F. for conversion of $C_9^+$ aromatics to BTX and fuel gas. The effluent of processing heavy aromatics is combined with the isomerizer effluent for passage to the usual high pressure separator from which hydrogen is recovered for recycle to both isomerization and heavy aromatics conversion. When operated within the specified temperature limits, the two reactors provide a blended stream such that a majority of the light hydrocarbons produced remain dissolved in the liquid withdrawn from the high pressure separator, permitting maintenance of high purity of recycle hydrogen with little or no discharge of that stream from the system. The combined liquids are then processed together through the normal distillation train such that isomerized xylenes are recycled to p-xylene separation together with xylenes which result from reaction in the heavy aromatics reactor. In similar fashion, unconverted heavy aromatics are recycled with fresh heavy aromatics from the isomerizer which result primarily from conversion of ethyl benzene. It will be seen that ethyl benzene in both effluents will recycle to the isomerizer with xylenes. When so operated, the combined system will yield only benzene, toluene and p-xylene together with light paraffins useable as fuel gas as major products. Preferably, a small quantity of very heavy dicyclic aromatics will be withdrawn to avoid accumulation of components conducive to high rates of coke formation on catalyst in the heavy aromatics reactor.

According to a preferred embodiment, toluene is separated from the combined reactor effluents and is recycled to the heavy aromatic reactor with the $C_9^+$ fraction. It is found that such toluene recycle can result in recovery of p-xylene at a level greater than total xylene content of the fresh feed to the system.

By the practice of this invention, the isomerizer and heavy aromatics reactor are caused to interact in a manner which results in a measure of interdependence of the two reactors in the sense that each affects the equilibrium in the other.

DESCRIPTION OF THE DRAWING

A system for practice of the invention is exemplified by the flow sheet of essential elements set out as the single FIGURE of the annexed drawing.

DESCRIPTION OF PREFERRED EMBODIMENTS

A fresh feed comprising a mixture of $C_8$ aromatics is introduced to the system by line 10 to mix with xylene recycle from line 11 and the mixture is passed to p-xylene recovery unit 12 from which p-xylene at high purity is withdrawn as the major product by line 13. Xylene recovery unit 12 will be of any type suited to the purpose, for example the fractional crystallization equipment described in Machell et al U.S. Pat. No. 3,662,013.

The effluent from recovery unit 12 is constituted by $C_8$ aromatics lean in p-xylene and containing the ethyl benzene, o-xylene and m-xylene present in the feed to the recovery unit 12. That effluent passes by line 14 to isomerizer 15 in admixture with hydrogen supplied by line 16. Isomerizer 15 is operated in accordance with the disclosure of the Morrison U.S. Pat. No. 3,856,872, but at relatively mild conditions of 550° – 700° F. These relatively low temperatures conserve xylene content while isomerizing the xylenes to near equilibrium ratios, but with less conversion of ethyl benzene than can be achieved at more severe reaction conditions. As will be seen from data presently to be described, the gaseous paraffin content of the isomerizer effluent at these conditions is essentially propane which remains with the liquid phase in a flash drum or high pressure separator 17 to which the isomerizer effluent passes by line 18 after admixture with products of heavy aromatics processing from line 19 and cooling in heat exchanger 20. Flash drum 17 operates at about 100° F. at pressure resulting from conditions of reaction in isomerization and heavy aromatics processing whereby hydrogen and a small amount of light hydrocarbons are separated as gas to be recycled via line 21. At the conditions of operation, much of the light paraffin content of feed to flash drum 17 remains dissolved in the liquid portion withdrawn by line 22. Makeup hydrogen to replace that consumed in the system may be added conveniently to the vapor space of flash drum 17 from line 23.

The liquid fraction from flash drum 17 passes by line 22 to a fractionation column 23 where it is split to take $C_8^+$ hydrocarbons as bottoms and lighter material overhead by line 24 to a condenser 25 from which light ends are removed by line 26 for appropriate disposal, preferably as fuel gas. The liquid fraction from condenser 25 is transferred by line 27 to toluene tower 28 from which high purity toluene is withdrawn as bottoms by line 29. Overhead from tower 28 is fed by line 30 to benzene tower 31 from which benzene is withdrawn at high purity by line 32 while overhead of light gases in line 33 is suitable for use as fuel gas. Alternatively, the liquid in line 27 may be transferred to an existing distillation train for recovery of benzene and toluene from extracted BTX.

Bottoms from splitter 23 is transferred by line 34 to xylene splitter 35 from which overhead is composed of the $C_8$ aromatics from isomerization and heavy aromatics processing and is recycled to p-xylene recovery unit 12 by line 11 as previously described.

A minor portion of heavy aromatics, say dicyclics, is discharged from the system as bottoms of splitter 35 by line 36. A $C_9^+$ fraction is taken from xylene splitter 35 as a side stream at line 37 for recycle to heavy aromatics processing in reactor 38 after mixing with recycle hydrogen from line 39. Conditions in reactor 38 are essentially those described in Brennan and Morrison U.S. Pat. No. 3,945,913, but at the upper portion of the temperature range there stated, namely 750° to 900° F. and hydrogen recycle rate of 2 to 10 moles of hydrogen per mole of hydrocarbon charge. The catalyst for this reaction may be any solid porous acidic catalyst, but is preferably an aluminosilicate zeolite having a silica/alumina ratio greater than 12 and a constraint index of 1 to 12 as described in U.S. Pat. No. 3,968,024 (Gorring and Shipman) granted July 6, 1976, the disclosure of which is incorporated herein by this reference.

In a preferred form of the invention, toluene from tower 28 is added to the feed for heavy aromatics reactor 38 by recycle line 40. Alternatively, toluene may be withdrawn as a product at line 41.

The catalyst in isomerization reactor 15 is of the same nature as that preferred for reactor 38, to wit an alumino-silicate zeolite having a silica/alumina ratio of at least 12 and a constraint index between 1 and 12.

Yields from typical operations according to the invention have been determined by computer simulation utilizing models of the several process steps which have been found to accurately reflect results obtained by conducting those steps. Those yields are reported in the Examples below.

EXAMPLE 1

In an operation according to the preferred embodiment in which toluene is recycled to the heavy aromatics reactor, fresh feed was constituted by 10,000 barrels per day of a $C_8$ aromatic fraction containing 19.2% ethyl benzene, 18.2% p-xylene, 42.4% m-xylene and 20.2% o-xylene. The net products withdrawn from the system consisted of 9.11% (by weight based on charge) of fuel gas containing paraffins of 5 or less carbon atoms, 10.52% benzene, 81.11% p-xylene and 0.05% heavy aromatics. The yield of p-xylene was found to be 100.38% of the total xylenes in the fresh feed.

Xylene recycle was added to fresh feed at the rate of 56,824 barrels per day and consisted of 0.2% toluene, 14.2% ethyl benzene, 20.4% p-xylene, 45.7% m-xylene, 19.3% o-xylene and 0.1% $C_9$ aromatics. The blend of fresh feed and xylene recycle was supplied to a crystallizer operated for recovery of p-xylene at the rate of 60 mole % recovery of p-xylene in the feed. Crystallizer effluent was mixed with 1 to 4 moles of hydrogen (85% purity) per mole of hydrocarbon and reacted over NiHZSM-5 at 250 psig, 615° F. and weight hourly space velocity of 8.5. This resulted in p-xylene approach to equilibrium of 99.88% at ethyl benzene disappearance of 20.05% and net xylene loss of 1.26%.

The stream from the xylene splitter 35 by line 37 was at the rate of 3284 barrels per day containing 0.1% ethyl benzene, 4.4 xylenes, 38.4% $C_9$ aromatics and 57% $C_{10}^+$ aromatics. That stream was blended with 1405.4 barrels per day of toluene recovered in the system and mixed with 2 moles of hydrogen per mole of hydrocarbon and processed over HZSM-5 at 850° F., 250 psig and a weight hourly space velocity of one.

Effluents of the two reactors were blended for feed to flash drum 17 and the materials processed through the distillation train in the manner described above.

Composition of significant streams is shown in the following table:

| Source | Composition of Effluent Streams | | |
|---|---|---|---|
| | Isomerizer | Heavy Aromatics Reactor | High Pressure Separator |
| $C_1$ wt. % | 0.0 | 2.7 | 0.2 |
| $C_2$ | 0.0 | 3.3 | 0.3 |
| $C_3$ | 0.1 | 10.4 | 0.9 |
| $C_4$ | 0.0 | 0.4 | 0.1 |
| $C_5$ | 0.0 | 0.0 | 0.0 |
| $C_6^+$ non-aromatic | 0.0 | 0.0 | 0.0 |
| Benzene | 1.4 | 5.5 | 1.7 |
| Toluene | 0.6 | 24.1 | 2.4 |
| Ethyl benzene | 13.6 | 2.0 | 12.7 |
| p-xylene | 19.4 | 4.0 | 18.3 |
| m-xylene | 43.6 | 8.3 | 41.0 |
| o-xylene | 18.6 | 3.9 | 17.4 |
| $C_9$ Aromatic | 0.7 | 18.9 | 2.1 |
| $C_{10hu\ +}$ Aromatic | 1.9 | 16.3 | 3.0 |
| Heavy Aromatic | 0.0 | 0.1 | 0.0 |

EXAMPLE 2

Data were computed on a run like that of Example 1 except that toluene was recovered as a product instead of being recycled to the heavy aromatics reactor as in Example 1. The products consisted of 9.05% of fuel gas, 8.18% benzene, 5.69% toluene, 77.83% p-xylene and 0.03% heavy aromatics.

I claim:

1. In a process for recovery of p-xylene from a fresh feed of eight carbon atom alkyl aromatic compounds including ethyl benzene and the three xylene isomers by separating p-xylene from a mixture of said fresh feed with xylene recycle as hereinafter defined, subjecting the mixture depleted of p-xylene to isomerization by contact with hydrogen in the presence of a catalyst consisting essentially of a metal having hydrogenation/dehydrogenation catalyst properties and a crystalline aluminosilicate zeolite having a silica/alumina ratio of at least 12 and a constraint index of about 1 to about 12, separating hydrogen from the isomerate so produced, recycling separated hydrogen to the feed to the isomerization step, separating $C_9^+$ and $C_7^-$ hydrocarbons from the hydrogen free isomerate and adding the remaining $C_8$ hydrocarbons to said fresh feed as said xylene recycle;

the improvement which comprises conducting said isomerization at a temperature of about 550° to 700° F., admixing the separated $C_9^+$ hydrocarbons with hydrogen, contacting the hydrogen/$C_9^+$ mixture with a porous acidic solid catalyst at a temperature of about 750° to 900° F., blending the product of such contacting with said isomerate, and recycling a portion of said separated hydrogen to admixture with said $C_9^+$ hydrocarbons.

2. The process of claim 1 wherein toluene is separated from said $C_7^-$ hydrocarbons and added to said $C_9^+$ hydrocarbons for contact with said porous acidic solid catalyst.

3. The process of claim 1 wherein said porous acidic solid catalyst is a crystalline aluminosilicate zeolite having a silica/alumina ratio of at least 12 and a constraint index of about 1 to about 12.

4. The process of claim 1 wherein said zeolite is ZSM-5.

5. The process of claim 3 wherein said porous acidic solid catalyst is ZSM-5.

* * * * *